United States Patent [19]
Nomura et al.

[11] Patent Number: 5,496,717
[45] Date of Patent: Mar. 5, 1996

[54] RESTRICTION ENDONUCLEASE

[75] Inventors: Yoshiko Nomura, Kyoto; Fusao Kimizuka, Ohmihachiman; Yoshizumi Ishino, Takatsuki; Ikunoshin Kato, Uji, all of Japan

[73] Assignee: Takara Shuzo Co., Ltd., Kyoto, Japan

[21] Appl. No.: 348,961

[22] Filed: Nov. 28, 1994

[30] Foreign Application Priority Data

Nov. 30, 1993 [JP] Japan .................................. 5-323459

[51] Int. Cl.⁶ ................................ C12N 9/22; C12N 9/16
[52] U.S. Cl. .......................... 435/199; 435/196; 435/814
[58] Field of Search .................................. 435/199, 196, 435/814

[56] References Cited

U.S. PATENT DOCUMENTS

| | | | |
|---|---|---|---|
| 4,840,901 | 6/1989 | Grosskopf et al. | 435/91 |
| 5,134,069 | 7/1992 | Kaluza et al. | 435/91 |
| 5,183,747 | 2/1993 | Kaluza et al. | 435/91 |

OTHER PUBLICATIONS

Sigma Catalog: Products for Molecular Biology (1992) pp. 7–35, Sigma Chemical Co., St. Louis, Mo.

Housekin no doutei jikkenhou (Experimental methods for the identification of actinomycetes), first edition, by The Society for Actinomycetes, Japan (The Secretariat of The Society for Actinomycetes, Japan, 1985), pp. 58–87 and 131–139.

Biseibutu no kagaku bunrui jikkenhou (Experimental method for chemical classification of microorganisms), First Edition, by K. Komagata (Gakkai syuppan Center 1982), pp. 143–155.

Atarashii bunruigaku ni hansou suru saikin douteihou (Identification of microorganisms under new taxonomy), first edition, by E. Yabuuti et al., (Natane syuppan, 1987), pp. 79–81.

Primary Examiner—Marian C. Knode
Assistant Examiner—Jon P. Weber
Attorney, Agent, or Firm—Wenderoth, Lind & Ponack

[57] ABSTRACT

A new restriction endonuclease capable of recognizing the nucleotide sequence of the following formula 1 in double stranded DNA.

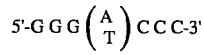

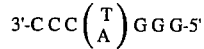

[Chemical formula 1]

and specifically cleaving it is disclosed.

The endonuclease may be made cultivating a strain of the genus Streptomyces (FERM BP-4836) capable of producing it.

5 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 29 bases
( B ) TYPE: nucleic acid
( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO:1:

AATTCCTCGA GAAGGACCC AACCATGGA 29

( 2 ) INFORMATION FOR SEQ ID NO:2:

( i ) SEQUENCE CHARACTERISTICS:
( A ) LENGTH: 29 bases
( B ) TYPE: nucleic acid
( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO:2:

GGAGCTCTTC CCTGGGTTGG TACCTTCGA 29

( 2 ) INFORMATION FOR SEQ ID NO:3:

( i ) SEQUENCE CHARACTERISTICS:
( A ) LENGTH: 17 bases
( B ) TYPE: nucleic acid
( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO:3:

GTTTTCCCAG TCACGAC 17

RESTRICTION ENDONUCLEASE

BACKGROUND OF THE INVENTION

1. Field of the Invention

This invention relates to a Class-II restriction endonuclease which recognizes a specific sequence of seven bases in a double stranded deoxyribonucleic acid (DNA) molecule and cleaves said DNA molecule at specific sites.

2. Description of Related Art

Restriction endonucleases are endonucleases that are capable of recognizing a specific sequence of bases in a DNA molecule and cleaving the DNA strands at specific sites. Many kinds of restriction endonucleases have so far been found. As a result of the progress in molecular genetics and biochemistry, DNA was proven to be the carrier of genetic information, and since then restriction endonucleases have been extensively used for various purposes, such as in the clarification of genetic diseases in gene manipulation.

Among them, class II restriction endonucleases, which can recognize specific DNA sequence and digest the DNA strand specifically within the sequence, are especially important and essentially used in genetic engineering techniques.

More than 300 class II restriction endonucleases have been isolated, however, many DNA sequences having no cognate restriction endonucleases (can not be recognized by any known restriction endonuclease) still remain. Therefore, it has been needed to make effort for discovering novel class II restriction endonucleases having ability to recognize and digest these sequences, so that researchers have more chance to cut their DNA at positions suitable for each experiment.

Moreover, restriction endonucleases with low cutting frequencies are more convenient for structural analyses of high molecular weight DNA such as genome analysis projects of several living things, and the discovery of the class II restriction endonucleases recognizing long DNA sequences more than six bases have been demanded.

SUMMARY OF THE INVENTION

The purpose of this invention is to provide a novel restriction endonuclease of class II having an ability to recognize and cut a new DNA sequence, which is suitable for genetic engineering research including the analysis of high molecular weight DNA.

In a first aspect of the this invention, there is provided a restriction endonuclease capable of specifically recognizing the nucleotide sequence of the following formula 1 in a DNA molecule and specifically cleaving the same,

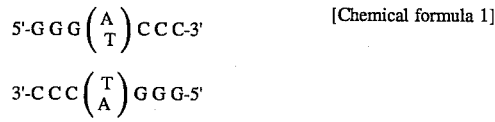

[Chemical formula 1]

(wherein A, G, T and C represent adenine, guanine, thymine and cytosine, respectively).

In a second aspect of the this invention, there is provided the reagents to be used in the genetic engineering method containing the restriction endonuclease described above.

In a third aspect of this invention, there is provided a process for producing the above restriction endonuclease, which comprises growing a microorganism belonging to the genus Streptomyces which is capable of producing the above endonuclease and recovering the endonuclease thus formed from the culture broth.

In a fourth aspect of the this invention, there is a microorganism belonging to the genus Streptomyces which capable of producing the above restriction endonuclease.

The Class-II restriction endonuclease of this invention may be any endonuclease that is capable of specifically recognizing and cleaving the above-mentioned nucleotide sequence, which endonuclease can be obtained by cultivating a strain capable of producing the same, a mutant of the above strain, or a recombinant prepared by isolating the gene coding for the production of said endonuclease and transforming it into a different kind of host organism by utilizing ordinary genetic manipulation techniques.

The actual strain producing the restriction endonuclease that recognizes the heptanucleotide sequence described above is Streptomyces sp. AH1825. This strain was isolated from soil which were collected and stored in inventors laboratories. The bacteriological characteristics are shown in Table 1.

TABLE 1

| Type of cell wall | Type I |
|---|---|
| L, L-diaminopimelic acid | + |
| meso-diaminopimelic acid | − |
| diaminobutyric acid | − |
| glycine | + |
| aspartic acid | − |
| ornithine | − |
| lysine | − |
| arabinose*1 | − |
| galactose*1 | + |
| Quinone | MK-9(H$_8$), MK-9(H$_6$) |
| Aerial mycelium*2 | + |
| Spore linkage*2 | + |

*1 Assumption by hydrolysis of the whole cells with sulfuric acid.
*2 Examination through a microscope.

The analysis of the cell wall composition was performed as described in the following three literatures, *Housenkin no doutei jikkenhou* (first edition) by The Society for Actinomycetes, Japan (The Secretariat of The Society for Actinomycetes, Japan, 1985), *Biseibutu no kagaku bunrui jikkenhou* (first edition) by K. Komagata (Gakkai syuppan center, 1982) and *Atarashii bunruigaku ni hansou suru saikin douteihou* (first edition) by E. Yabuuti et al., (Natane syuppan, 1987). The cell wall type of this strain was concluded to be type I. The analyses of the quinone component showed that this strain has menaquinones having 9 isoprene units with 6 or 8 of the saturated hydrogen in the multiprenyl strand. Moreover, from the morphological observation, the strain has aerial mycelium and spore linkage. From these analyses, this strain was identified as a species belonging to the genus Streptomyces.

The present strain was designated as Streptomyces sp. AH1825. This strain was deposited on Aug. 4, 1993 at National Institute of Bioscience and Human-Technology Agency of Industrial Science and Technology (1-3, Higashi 1 chome Tsukuba-shi Ibaraki-ken 305, JAPAN), under the accession number FERM P-13783, and on Oct. 17, 1994 this deposit was converted to deposit at National Institute of Bioscience and Human-Technology Agency of Industrial Science and Technology in accordance with the Budapest Treaty under the accession number FERM BP-4836.

The restriction endonuclease isolated from Streptomyces sp. AH1825 with recognition sequence of the seven bases has the properties as described above and is designated Sse 18251.

Detailed below is the process for producing restriction endonuclease Sse 18251.

DETAILED DESCRIPTION OF THE INVENTION

Any nutrients which the strain used assimilates to produce Sse 1825I may be added to the culture medium. Glucose, maltose, glycerol and others may be used as carbon source, while yeast extract, peptone, corn steep liquor, bouillon and others are suitable as nitrogen source. In addition, minerals and metal salts, such as phosphates, potassium salts and magnesium salts, may also be added.

The yield of Sse 1825I varies depending on culture conditions. Good results are generally obtained at a temperature in the range from 20° to 35° C. and at a pH in the range from 6 to 8; and the highest output is achieved by culture with aeration and agitation for one to three days. It is needless to say that optimal culture conditions should be selected case by case according to the strain used and the composition of culture medium.

Restriction endonuclease Sse 1825I produced by the process of this invention is chiefly accumulated in the microbial cells. The grown cells can be isolated from the culture broth, for example, by centrifugation. The endonuclease formed can be isolated and purified by using known techniques commonly employed for restriction endonuclease. For example, the collected microbial cells are dispersed in a buffer solution, and then broken down by ultrasonic treatment to allow extraction of the endonuclease.

After removal of the cell debris by ultracentrifugation, ammonium sulfate is added to the extract for salting out, the precipitate which is separated out is dissolved in a buffer solution A (containing 20 mM Potassium phosphate, pH 7.5, 10 mM 2-mercaptoethanol and 5% glycerol), and the solution is dialyzed against the same buffer solution. The dialyzate is then purified by ion exchange chromatography, molecular sieve chromatography or affinity chromatography, thus giving the restriction endonuclease of this invention.

The activity of this endonuclease was determined according to the method described below.

A substrate solution of the composition shown in Table 2 below was prepared.

TABLE 2

| | |
|---|---|
| 10 mM | Tris-HCl, pH 8.0 |
| 10 mM | MgCl$_2$ |
| 7 mM | 2-Mercaptoethanol |
| 100 mM | KCl |
| 1.0 µg | λ-DNA |

This solution (48 µl) as preheated to 37° C., the sample of Sse 1825I (2 µl) to be tested was then added to allow the enzymatic reaction to proceed at that temperature, and the reaction was stopped ten minutes later by addition of 5 µl of a terminator solution (1% SDS, 50% glycerol, and 0.02% Bromophenol Blue).

The reaction mixture was applied to a 0.7% agarose slab gel, and electrophoresis was conducted at a constant voltage of 10 V/cm for about one to two hours. The buffer solution used for electrophoresis was 90 mM Tris-borate buffer containing 2.5 mM EDTA (pH 8.3). DNA bands can be detected by UV irradiation if 0.5 µg/ml ethidium bromide is previously added to the gel. Electrophoresis was regarded as complete when the number and intensity of the bands for DNA fragments no longer changed.

The endonuclease activity which ensures complete digestion of 1 µg λ-DNA after one hour's reaction at 37° C. was defined as one unit.

Restriction endonuclease Sse 1825I has the physicochemical properties as described below.

(1) Action and substrate specificity

This endonuclease is capable of recognizing the nucleotide sequence of the following formula 1 in a double stranded DNA molecule and cleaving it at the arrow-marked sites.

[Chemical formula 1]

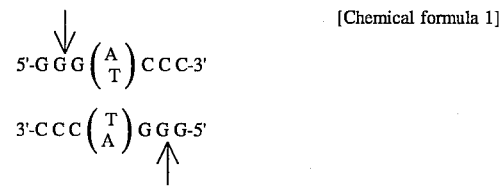

The nucleotide sequence recognized by restriction endonuclease Sse 1825I was determined as described below.

Restriction endonuclease Sse 1825I cleaved λ-DNA at one sites and Adenovirus-2 (AD-2) DNA (produced by Bethesda Research Laboratories) at eight sites, but failed to cleave pUC18, M13mp18, SV40, Col EI, pBR322 and φX174 DNAs.

From the size of each digested DNA fragment, in addition to the cutting frequencies of the DNA molecules as described above, this endonuclease was expected to recognize the nucleotide sequence of the following formula 2 in the DNA molecule.

[Chemical formula 2]

The nucleotide sequence of seven bases shown above includes five bases (formula 3) of Ava II restriction endonuclease recognition sequence.

[Chemical formula 3]

Therefore, one experiment was performed, in which λ-DNA and AD-2 DNA were digested with Ava II before digestion with Sse 1825I. The resulting electrophoretic patterns of these DNA fragments were exactly same as those Sse 1825I single digestion. From these results, it was concluded that the restriction endonuclease Sse 1825I recognizes the nucleotide sequence shown in the formula 2.

To determine the cutting site of the Sse 1825I, oligonucleotides of the following formula 4 (SEQ ID NO:1) and formula 5 (SEQ ID NO:2) containing its recognition sequence were synthesized by the DNA synthesizer, and inserted into pUC118 and pUC119 after annealed for forming double strand.

[Chemical formula 4]

5'-AATTCCTCGAGAAGGGACCCAACCATGGA-(SEQ ID NO:1)

[Chemical formula 5]

5'-GGAGCTCTTCCCTGGGTTGGTACCTTCGA-(SEQ ID NO:2)

Single stranded DNAs were prepared from the resulting plasmids by usual protocol. DNA primer of the following formula 6 (SEQ ID NO:3) that can bind the flanking region of the multi cloning site of the plasmids.

[Chemical formula 6]

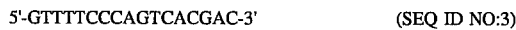

5'-GTTTTCCCAGTCACGAC-3'         (SEQ ID NO:3)

This primer was annealed with the single stranded DNAs prepared above, and extended by DNA polymerase from *Bacillus caldotenax* (BcaBEST DNA polymerase, produced by Takara Shuzo Co., Ltd.). The produced double stranded DNAs were digested with Sse 1825I, and the sizes of the digested DNA fragments were analyzed by denatured polyacrylamide gel electrophoresis. The products of the digestion reaction described above were detected as bands digested at the site indicated by an arrow in the following formula 7.

[Chemical formula 7]

5'-G G G A C C C-3'

Moreover, the digestion product was converted to three base longer one by blunting the terminal with T4 DNA polymerase (produced by Takara Shuzo Co., Ltd.). From these experiments, it was concluded that Sse 1825I recognizes the nucleotide sequence shown in formula 1 and digests the DNA at the site indicated by an arrow in formula 7.

(2) Optimal conditions for enzymatic activity a) Optimal temperature

The optimal temperature for Sse 1825I was approximately 37° C.

b) Optimal pH

The optimal pH for Sse 1825I was in the range from 7.0 to 9.0.

c) Salt concentration

The optimal salt concentration for Sse 1825I was in the range from 0 to 150 mM in the case of KCl.

d) $MgCl_2$ concentration

The enzymatic reaction of Sse 1825I was activated at a $MgCl_2$ concentration in the range from 5 mM to 20 mM.

(3) Determination of molecular weight

Molecular weight of Sse 1825I was determined for the native protein by equilibrium density gradient centrifugation. The density gradient was prepared by glycerol in the buffer solution as described in Table 3.

TABLE 3

| |
| --- |
| 10 mM Tris-HCl, pH 7.5 |
| 10 mM 2-Mercaptoethanol |
| 100 mM KCl |
| 10–25% Glycerol |

In a 5 ml tube, 4.8 ml of continuous 10–25% (top to bottom) gradient was prepared, and the Sse 1825I protein in 200 μl of the same buffer was sedimented through the gradient. Marker proteins (SDS-PAGE molecular weight standard low range, Bio-Rad Laboratories, Inc.) was sedimented through the same gradient, in parallel.

The gradient was centrifuged at 45,000 rpm at 4° C. for 21 hours in a swing rotor.

After centrifugation, fractions 250 μl were collected from the top of the gradient and fractions were numbered from 1 to 20.

These fractions were assayed for enzyme activity. The highest activity was detected in the fraction number 12. The sedimentation coefficient for the Sse 1825I protein was interpolated from the standard curve obtained from the analysis of marker proteins by SDS-PAGE after sedimentation.

An estimate of the approximate native molecular weight for Sse 1825I was calculated to be 60,000 to 75,000.

EXAMPLES

The following Example will further illustrate this invention but is not intended to limit its scope.

EXAMPLE 1

One hundred milliliters of a culture medium having the composition shown in Table 4 below was put in a 500 milliliter Erlenmeyer flask and sterilized by the method commonly employed. The grown cells of Streptomyces sp. AH1825 (FERM BP-4836), obtained by shake culture in a medium having the same composition as above at 30° C. for 48 hours, were collected from the culture broth by using a refrigerated centrifuge, and obtained 3.5 g of grown cells on wet basis from one hundred milliliters of the culture broth.

TABLE 4

| | |
| --- | --- |
| Glucose | 10 g |
| Yeast extract | 10 g |
| Polypeptone | 10 g |
| Sodium chloride | 5 g |
| Deionized water | 1 l |
| pH | 7.2 |

3.5 g of the microbial cells obtained above were suspended in 10 ml of buffer solution A, the suspension was treated in a ultrasonic crusher to break down the cell walls, and the resulting mixture was centrifuged (100,000× g, one hour) to remove the residue. To the supernatant (12 ml) thus obtained, was added ammonium sulfate to 80% saturation, the precipitate which separated out was collected by centrifugation and dissolved in buffer solution A, and the solution was dialyzed overnight against the same buffer solution as above.

The dialyzate was then adsorbed on 5 ml of phosphocellulose P11 (produced by Whatman Co.) packed in a column and previously equilibrated with buffer solution A. After washing with the same buffer as above, the adsorbed portion was eluted with buffer solutions A containing 0M to 1.0M KCl (linear concentration gradient technique).

The active fractions thus obtained were mixed together, the combined solution was analyzed for four hours against buffer solution A, and the dialyzate was once more adsorbed on 2 ml of heparine Sepharose (produced by Pharmacia Biotech Inc.) packed in a column and previously equilibrated with buffer solution A. After thoroughly washing with the same buffer as above, the adsorbed portion was eluted with buffer solutions A containing 0M to 1.0M KCl (linear concentration gradient technique), affording the standard sample of restriction endonuclease Sse 1825I.

This standard sample was free from any non-specific deoxyribonuclease or phosphatase.

The purification method described above gave 600 unit activity from 3.5 g of wet microbial cells.

The present invention provides a novel restriction endonuclease capable of recognizing and cleaving a sequence of seven bases in double stranded DNA molecules. The endonuclease of this invention is of great use in the field of genetic engineering, for example, for analysis of long chain DNA molecules and for other purposes.

We claim:

1. A purified restriction endonuclease (a) which specifically recognizes and which specifically cleaves a heptanucleotide consisting of the following double stranded deoxyribonucleotide sequence at the arrow sites:

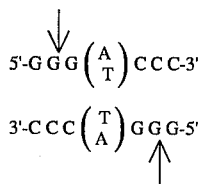

wherein A, G, T and C are adenine, guanine, thymine and cytosine, respectively;

(b) which has the following physicochemical properties:

(a) Optimal temperature: approximately 37° C.;
(b) Optimal pH: 7.0 to 9.0;
(c) Molecular weight: 60,000 to 75,000;

and (c) which can be recovered from Streptomyces sp. AH1825 deposited under accession number FERM BP-4836.

2. A process for producing the restriction endonuclease of claim 1, comprising culturing the Streptomyces sp. AH1825 in a nutrient media for a time and under conditions to produce the restriction endonuclease according to claim 1, and recovering the restriction endonuclease.

3. A restriction endonuclease isolated from Streptomyces sp. AH1825 deposited under accession number FERM BP-4836, which specifically recognizes and which specifically cleaves a heptanucleotide consisting of the following double stranded deoxyribonucleotide sequence at the arrow sites:

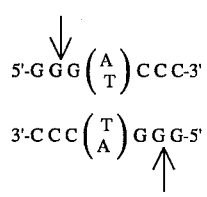

wherein A, G, T and C are adenine, guanine, thymine and cytosine, respectively.

4. The restriction endonuclease according to claim 3, having the following physicochemical properties:

(a) Optimal temperature: approximately 37° C.;
(b) Optimal pH: 7.0 to 9.0;
(c) Molecular weight: 60,000 to 75,000.

5. A process for producing the restriction endonuclease of claim 3, comprising culturing the Streptomyces sp. AH1825 in a nutrient media for a time and under conditions to produce the restriction endonuclease according to claim 3, and recovering the restriction endonuclease.

* * * * *